United States Patent [19]

Goldberg et al.

[11] Patent Number: 5,376,400
[45] Date of Patent: Dec. 27, 1994

[54] COMBINED PLASMA AND GAMMA RADIATION POLYMERIZATION METHOD FOR MODIFYING SURFACES

[75] Inventors: Eugene P. Goldberg; Ali Yahiaoui, both of Gainesville, Fla.; James Burns, Holliston, Mass.

[73] Assignee: University of Florida Research Foundation, Inc., Gainesville, Fla.

[21] Appl. No.: 3,682

[22] Filed: Jan. 13, 1993

Related U.S. Application Data

[63] Continuation of Ser. No. 602,144, Oct. 24, 1990, abandoned.

[51] Int. Cl.$^5$ .......................... A61F 2/02; B05D 3/04; A61M 1/00; A61M 25/00
[52] U.S. Cl. .................................. 427/2.24; 427/2.11; 427/2.3; 427/299; 427/322; 427/327; 427/498; 427/501; 427/507; 427/536; 427/539
[58] Field of Search ............... 427/2, 536, 535, 538, 427/539, 495, 496, 498, 501, 507, 322, 327, 299, 488

[56] References Cited

U.S. PATENT DOCUMENTS

| | | | |
|---|---|---|---|
| 3,853,657 | 12/1974 | Lawton | 427/35 |
| 4,022,925 | 5/1977 | Reuter et al. | 427/35 |
| 4,072,769 | 2/1978 | Lidel | 427/488 |
| 4,310,614 | 1/1982 | Connell et al. | 427/38 |
| 4,407,846 | 10/1983 | Machi et al. | 427/498 |
| 4,707,380 | 11/1987 | Hashimoto et al. | 427/322 |
| 4,743,327 | 5/1988 | DeHaan et al. | 427/41 |
| 4,806,382 | 2/1989 | Goldberg et al. | 427/2 |
| 4,822,451 | 4/1989 | Ouderkirk et al. | 427/322 |
| 4,838,873 | 5/1989 | Benz et al. | 427/488 |
| 4,921,723 | 5/1990 | Nichols et al. | 427/41 |
| 4,938,827 | 7/1990 | Leach et al. | 156/272.6 |
| 4,955,901 | 9/1990 | Nishiguchi et al. | 623/6 |
| 4,961,954 | 10/1990 | Goldberg et al. | 427/2 |
| 4,980,196 | 12/1990 | Yasuda et al. | 427/327 |
| 5,064,679 | 11/1991 | Ito et al. | 427/322 |
| 5,069,967 | 12/1991 | Yokoyama et al. | 427/41 |
| 5,094,876 | 3/1992 | Goldberg et al. | 427/2 |
| 5,100,689 | 3/1992 | Goldberg et al. | 427/507 |
| 5,132,108 | 7/1992 | Narayanan et al. | 427/41 |
| 5,169,675 | 12/1992 | Bartoszek-Loza et al. | 427/539 |
| 5,234,723 | 8/1993 | Babacz | 427/536 |
| 5,280,084 | 1/1994 | Paul | 427/299 |

FOREIGN PATENT DOCUMENTS

2755189  6/1979  Germany ........................ 427/493

*Primary Examiner*—Shrive Beck
*Assistant Examiner*—Diana Dudash
*Attorney, Agent, or Firm*—Kerkam, Stowell, Kondracki & Clarke

[57] ABSTRACT

A method for modifying the surface of a material by:
a. exposing the surface to a glow discharge plasma to activate the surface;
b. exposing the surface to an ethylenically unsaturated monomer or mixture of monomers; and
c. irradiating the activated surface with gamma radiation or electron beam radiation in the presence of the ethylenically unsaturated monomer to form a graft polymerized coating thereon.

18 Claims, 7 Drawing Sheets

COMBINED PLASMA AND GAMMA RADIATION POLYMERIZATION METHOD FOR MODIFYING SURFACES

This is a continuation, of application Ser. No. 07/602,144, filed Oct. 24, 1990, abandoned.

BACKGROUND OF THE INVENTION

1. Field of the Invention

The present invention relates to a method for modifying the surfaces of materials to impart desired characteristics thereto.

2. Prior Art

In selecting materials for constructing articles, the artisan is often faced with a perplexing dilemma. A specific material may meet most of the requirements of the proposed application, such as strength, weight, density, structure, machinability, electromagnetic properties, etc.; however, its surface characteristics may render it unsuitable. For example, studies have shown that the surgical implantation of ocular implants such as intraocular lenses (IOL), etc., results in the loss of significant corneal endothelial tissue unless great care is taken to ensure a lack of contact between the device and the endothelium. Most ocular implants are constructed of hydrophobic polymethyl methacrylate (PMMA) polymers because of their superior optical qualities, resistance to biodegradation, etc. It has been found, however, that PMMA surfaces adhere to endothelial cells upon even casual contact and that separation of the surface therefrom results in a tearing away of the endothelial tissue adhered to the polymer surface. Similar adhesive interactions with other ocular tissues, i.e., the iris, can also cause adverse tissue damage. Other hydrophobic polymers which are used or have been proposed for use in ocular implants (i.e., polypropylene, polyvinylidene fluoride, polycarbonate, polysiloxane) also can adhere to ocular tissue and thereby promote tissue damage.

It is well documented in the prior art that a significant disadvantage inherent in PMMA IOLs resides in the potential for long-term abrasive interactions with sensitive tissues such as the iris, ciliary sulcus, etc., and that even brief contact between the corneal endothelium and hydrophobic polymer surfaces, i.e., PMMA, can result in extensive damage to the endothelium. See Katz et al, *Trans. Am. Acad. Ophth.*, Vol. 83, p. 204–212 (1977).

Since it is extremely difficult to avoid any contact between implant surfaces and sensitive tissue surfaces such as ocular tissue during surgical procedures, efforts have been undertaken in ocular surgery to modify ocular implant surfaces, i.e., PMMA, to reduce the tendency thereof to adhere to and damage the corneal endothelium.

Ocular implant surfaces have been coated with various hydrophilic polymer solutions or temporary soluble coatings such as methylcellulose, polyvinylpyrrolidone, etc., to reduce the degree of adhesion between the implant surfaces and endothelial tissue cells. While offering some temporary protection, these methods have not proven entirely satisfactory, since such coatings complicate surgery, do not adhere adequately to the implant surfaces, become dislodged or deteriorate after implantation, dissolve away rapidly during or soon after surgery, or may produce adverse post-operative complications. Moreover, it is difficult to control the thicknesses and uniformity of such coatings.

Various surface modification techniques have already been proposed, and some of them are in use. For instance, surface grafting of hydrophilic monomers onto hydrophobic polymers has been achieved by photo-induced [Oster et al, *J. Polym. Sci.*, Vol. 26, p. 233 (1957); Oster et al, Ibid., Vol. 34, p. 67 (1959); Tazuke et al, *J. Polym. Sci.*, Polym. Lett. Edn. 16, p. 497 (1978); and Ogiwara et al, *J. Appl. Polym. Sci.*, Vol. 23, p. 2397 (1979)] and radiation-induced polymerization [Jansen et al, *J. Biomed. Mater. Res.*, Vol. 19, p. 1085 (1985); Boffa et al, *J. Biomed. Mater. Res.*, Vol. 11, p. 317 (1977)]. However, all these methods suffer major limitations, i.e., grafting reactions are not confined to the outer substrate surface layers; grafting reaction time is too long; the coatings obtained are generally only physically absorbed on the substrate surface; and, finally, because of the relatively high penetration power of the radiation required for grafting, permanent chemical and structural changes such as cross-linking and degradation are commonly encountered [Mukherjee et al, *J. Macromol. Sci. -Rev. Macromol. Chem. Phys.*, Vol. C26(3), p. 475 (1986)].

In addition to polymeric ocular implants, there are also a wide variety of metallic, ceramic and polymeric medical instruments, devices and implants which could be beneficially surface modified to yield non-adherent tissue-protective and more blood-compatible hydrophilic polymer grafted surfaces. Improved methods and materials for hydrophilic polymer surface modification of various polymeric instruments, devices, etc., have been set forth in copending application Ser. No. 07/592,482, filed Oct. 5, 1990, now U.S. Pat. No. 5,100,689. However, certain polymer substrates, i.e., fluorocarbon polymers, and especially metal and ceramic substrates, are extremely resistant to effective grafting of uniform, highly adherent surface modifications by the major methods available, i.e., gamma radiation polymerization grafting and glow discharge plasma polymerization.

Glow discharge plasma (GDP) has been extensively studied for surface modification of biomedical polymers (Yasuda, in *Plasma Polymerization*, Academic Press, Inc. (1985); Kim et al, *CRC Crit. Rev. in Biocomp.*, Vol. 1, p. 229 (1985); Ratner et al, in *Trans. 2nd World Cong. Biomaterials*, Washington, D.C. (1984)). GDP may be achieved most commonly by radio frequency induction, or by DC discharge or microwave methods and has been used in two primary ways: 1) surface etching and/or oxidation by plasma treatment, and 2) plasma thin film polymerization and deposition. GDP induced by an inductively coupled radio frequency current (RF-GDP) is a high-energy state of ionized gases formed by passing gas or vapor molecules through a high-energy field. The resulting activated species possess energy to chemically alter the surface of a substrate placed in the GDP by generating activated surface species such as radicals or ion radicals. When exposed to air, these radicals or other activated sites can also combine with oxygen to form sites for further chemical reaction and polymerization with various vinyl monomers. Furthermore, monomers present in the plasma may be activated and graft polymerized to activated sites on the substrate. Under GDP conditions, even relatively unreactive compounds such as benzene, toluene, perfluoropropane, etc., which are not vinyl monomers may also be sufficiently activated to enable polymer-forming reactions.

Observations indicate that when hydrophobic polymers, such as FEP (Teflon), PC (polycarbonate), PMMA (polymethylmethacrylate), PDMSO (polydimethylsiloxane), PP (polypropylene), etc., are placed in a plasma even at relatively low power and for short exposure times and contact traces of oxygen, they become more hydrophilic due to surface oxidation. It has also been demonstrated that many polymers can be reduced or oxidized depending upon GDP conditions, thus altering their surface properties (Clark et al, J. Polym. Sci., Polym. Chem. Edn. 21p. 837 (1983).

Plasma treatment can cause chain scission, ablation, cross-linking, oxidation and other reactions to a depth of 50-100 Å or more depending on the substrate and experimental conditions [Wu et al, in Polymer Interphase and Adhesion, Chap. 9, p. 298, Marcel Dekker, New York (1982)].

The case of gamma polymerization alone has also been extensively studied for surface grafting of hydrophobic polymers [Boffa, supra; Hegazy et al, J. Appl. Polym. Sci., Vol. 26, p. 3117 (1981); Mukherjee et al, J. Appl. Polym. Sci., Vol. 30, p. 2643 (1985); Hoffman et al, Arch Phys. Chem., Vol. 22, p. 362 (1983)]; yet this method, by itself, is not always satisfactory. In addition to the problems mentioned earlier, gamma irradiation of substrate and monomer causes solution polymerization as well as grafting onto substrate. Grafting is dependent on the prevalence of excited surface species such as radicals generated by gamma radiation, which in turn is dependent upon the energy required to form such activated species in a particular substrate. Therefore, substrates with high activation energies for radical formation relative to monomer solutions do not easily graft by gamma polymerization before extensive solution polymerization and gelation occurs, making sample removal and washing impractical.

An improved and efficient method for the gamma-irradiation induced graft polymerization coating of the surfaces of ocular implants constructed of polymethylmethacrylate and other ocular implant polymers is disclosed in U.S. Pat. No. 4,806,382.

Although some polymeric substrates may be surface modified under certain conditions of gamma radiation graft polymerization, metallic and ceramic substrates pose extreme difficulties because low gamma radiation energy and the impermeability of such materials to monomeric molecules make such surface polymerization grafting impractical, leading to non-uniform, non-adherent structures.

The present invention comprises a novel surface grafting technique which overcomes all of the above problems. The technique is based on a combination of glow discharge plasma pretreatment of the solid substrate, followed by low dose gamma radiation or electron beam radiation initiated grafting in the presence of polymerizable monomer(s).

Although this combination of GDP and gamma or electron beam radiation graft polymerization represents a generally improved technique for polymer substrates, it is a uniquely effective process, heretofore unavailable, for the production of polymeric surface graft modifications of metal and ceramic substrates.

Only a few attempts have been reported in literature which employed plasma treatment combined with other treatments in order to induce grafting [Bamford et al, Polymer., Vol. 2, p. 277 (1961); Bazkin et al, J. Bioeng., Vol. 2, p. 527 (1978)]. Generally, these methods are based on decomposition of surface peroxides to radicals by heat treatment which initiates graft polymerization. However, heating up to 135° C. was sometimes required [Bamford, supra]. This temperature is beyond the glass transition temperature of a large number of polymers. Therefore, such a process cannot be used for surface grafting, especially for biomedical devices such as acrylic intraocular lenses, where shape and dimensional stability are very important. In 1971, Bradley and Fales reported another process based on the plasma-induced graft copolymerization of acrylic acid onto synthetic fibers [Bradley et al, Chemtech., p. 232, April 1984]. Grafting was induced by the surface radicals present on the plasma treated fibers. The grafting yields were generally relatively low and no grafting of other monomers was attempted. In contrast, the combined use of GDP surface modification with gamma graft surface modification represents a novel method for the preparation of improved polymer graft surfaces on polymers, metals and ceramics.

It is an object of the present invention to provide a generally applicable method for modifying the surface characteristics of a wide variety of materials not subject to the above-noted problems and disadvantages.

It is a further object of the invention to provide novel articles having modified surfaces, thereby enabling their efficient use in applications for which they were not previously suited.

SUMMARY OF THE INVENTION

The above and other objects are realized by the present invention which provides a method for modifying the surface of a material, the surface being capable of forming activated sites upon exposure to GDP, comprising:

a) exposing the surface to GDP such as RF-GDP or microwave GDP of sufficient power for a time required to activate and/or excite the surface of the material and, optionally, subsequently exposing the surface to air or oxygen to thereby form peroxy or hydroperoxy groups or other chemically reactive atomic or molecular species on the surface;

b) exposing the surface to a solution of an ethylenically unsaturated monomer or mixtures thereof capable, via the ethylenic unsaturation, of gamma- or electron beam-irradiation induced polymerization and covalent bonding to active surface species resulting from the GDP surface treatment; and c) irradiating the surface in the presence of the above unsaturated monomer solution with gamma or electron beam radiation to form a polymerized, chemically grafted surface modification from the monomer or mixture of monomers via the ethylenic unsaturation, the polymerization being initiated by the gamma or electron beam radiation, GDP activated sites, active surface oxygen-containing groups, or a combination thereof, wherein the graft polymerization is conducted under the following conditions:

i) monomer concentration in the solution in the range of from about 0.1% to about 50%, by weight;

ii) total gamma or electron beam dose in the range of from about 0.001 to less than about 0.5 Mrad; and iii) gamma dose rate in the range of from about 10 to about 2500 rads/min., or electron beam dose rate in the range of from about 10 to about $10^8$ rads/min.

The invention further provides an article of commerce manufactured at least in part from a material produced by the above-described method.

DETAILED DESCRIPTION OF THE INVENTION

Figure 1:
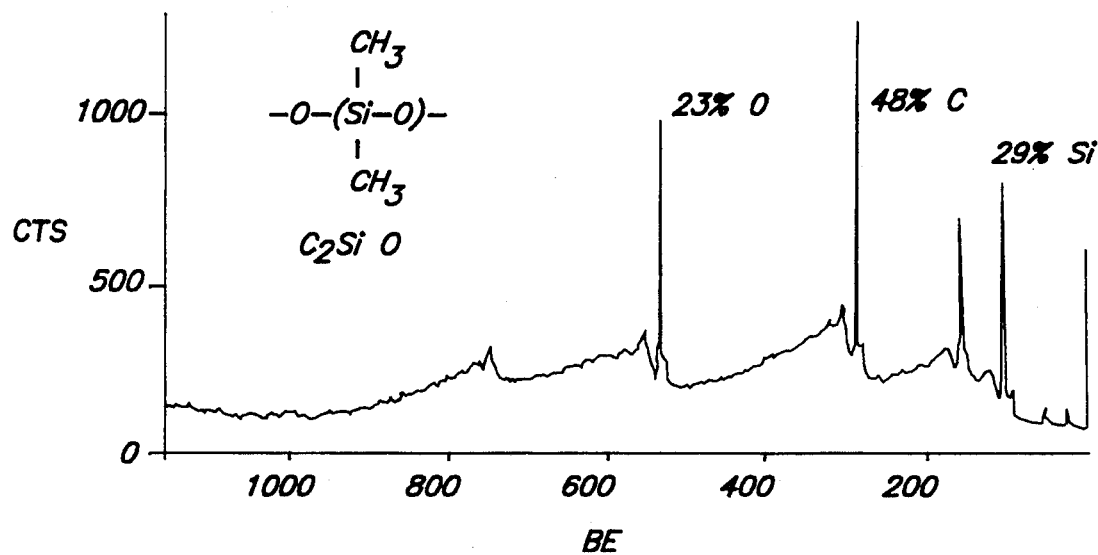

The present invention is predicated on the discovery that GDP treatment of the surfaces of materials followed by gamma or electron beam radiation induced polymerization surface modification, wherein the reaction parameters of each are carefully controlled, can be applied to a surprisingly wide variety of materials to alter the surface characteristics thereof without affecting the bulk or other properties of the material.

Moreover, the method is relatively simple to operate and is highly efficient and economical.

The method produces materials heretofore unknown which possess combinations of bulk and surface properties which render them invaluable in constructing articles having numerous uses.

The gamma radiation induced graft polymerization coating methods described in U.S. Pat. No. 4,806,382, the entire disclosure of which is incorporated hereby by reference, are suitable for forming hydrophilic coatings on certain hydrophobic polymeric surfaces. Conditions must be carefully controlled, however, to ensure successful preparation of uniform, permanent, strongly adherent surfaces and to minimize excessive solution polymerization of the monomer. Furthermore, using gamma radiation graft polymerization alone with metals and ceramics, which are relatively impermable to monomer diffusion and relatively unreactive chemically, uniform, adherent, permanent, chemically bound surface polymer grafts are extremely difficult to prepare.

It will be understood by those skilled in the art that electron beam radiation will also induce graft polymerization. Therefore, electron beam radiation of energies equivalent to that described herein for gamma radiation may be substituted for gamma radiation in the practice of the method of the invention. Electron beam voltages in the range of from about 50 KeV to about 10 MeV may be employed at currents of from about 5 mA to about 100 mA. For electron beam initiated polymerization grafting, conditions which produce dose rates substantially higher than from gamma craft polymerization, i.e., in the range of from about 10 to about $10^8$ rads/min. or more, may be employed. Accordingly, the term "gamma graft polymerization" as used herein is intended to also encompass "electron beam radiation graft polymerization."

On the other hand, the combined plasma/gamma process of the invention is unusual and surprisingly practical and effective for surface polymer grafting of polymers, metals and ceramics yielding uniform polymeric surface modifications with minimal solution polymerization complications. This is due to the fact that the plasma surface treatment activates and induces grafting sites which are available for subsequent surface graft polymerization by gamma irradiation. Thus, compared to gamma graft polymerization alone on polymer substrates, grafting will occur more readily and more extensively because of the prior plasma activation and permits gamma grafting under mild conditions without substantial solution polymerization. Moreover, for metals and ceramics which are resistant to effective surface graft polymerization, the initial plasma activation uniquely creates surface grafting sites for subsequent gamma graft polymerization which has heretofore been difficult to achieve.

The gamma-irradiation or electron beam induced graft polymerization of monomers on surfaces to form optimum graft polymer surface modifications thereon comprises carrying out the graft polymerization in an aqueous solution under specific combinations of the following conditions:

a) monomer concentration in the range of from about 0.1 to about 50%, by weight;

b) total gamma dose or electron beam dose in the range of from about 0.001 to about 0.50 Mrad;

c) gamma dose rate in the range of from about 10 to about 2500 rads/min. or electron beam dose rate in the range of from about 10 to about $10^8$ rads/min.

Optimally, the method may also be carried out under one or more of the following conditions:

d) substantially excluding free oxygen from the aqueous graft polymerization solution;

e) maintaining the thickness of the surface graft in the range of from about 100 Å to about 150 microns or more;

f) including a free radical scavenger in the graft polymerization solution; and g) including a swelling solvent for polymeric substrates or exposing polymeric substrates to monomers or monomer solutions for an extended time sufficient to allow diffusion of monomer into the substrate.

The improved process conditions and parameters of this invention which are necessary to produce useful surfaces modified by gamma-irradiation induced graft polymerization include: % monomer, gamma dose, dose rate, penetration time or swelling time of monomer into the substrate prior to polymerization and oxygen (air) degassing. Other optimal process conditions include catalysts, free radical scavengers, polymer swelling solvents and temperature. The solution polymer molecular weight and M.W. distribution, the % conversion and residual monomer, the graft polymer thickness and surface properties, etc., are process results which can change markedly as the process variables change. For example, the surface modification achieved for PVP on PMMA will be different when using 10% monomer and 0.1 Mrad if prepared at low-dose rate rather than high-dose rate since low dose rates (slower polymerization) often favor higher molecular weights. Similarly, degassed oxygen-free reaction media result in improved grafts at much lower doses. The presence of free radical scavengers such as copper or iron salts or organic reducing agents (i.e., ascorbic acid) also greatly influences other process parameters, generally reducing solution polymer molecular weight and preventing solution gelation at high monomer concentrations.

Each of the above-described process conditions and parameters may be varied within the ranges discussed below to produce certain specific combinations which are particularly advantageous for a particular surface:

a) Monomer concentration: Increasing hydrophilic monomer concentration often increases polymer mol. wt. in the graft solution and reduces contact angle (C.A.), i.e., renders the surface more hydrophilic.

In general, monomer concentrations in the range 0.1–50% are preferred depending on other parameters. For example, below 0.1%, even at low-dose rate and high-dose, grafting is inefficient and C.A. below 30°–40° is not obtained. At monomer concentrations greater than 20–30%, effective grafting without solution polymer gelation requires low doses and use of free radical scavengers. Monomer concentrations greater than 50% are feasible, but not preferred, since high concentrations of radical scavengers must be used and polymer mol. wts. and monomer conversion are lowered significantly by their use.

b) Dose: In general, increasing total gamma dose increases mol. wt. of the polymer and reduces C.A.. However, an important practical limit exists in that at higher doses, lower dose rates and higher monomer concentrations, reaction media become extremely viscous or form gels which are very difficult to wash and to remove (e.g., about 0.25 Mrad and 10% monomer at 309 rads/min.).

c) Dose rate: Decreasing dose rate increases solution polymer M.W. The C.A. also tends to go down at lower dose rates.

d) Solution Polymer Mol. Wt.: Increasing $M_v$ is often associated with lower C.A. grafts. However, $M_v$ greater than 5,000,000 or gels are generally impractical for grafting because of washing problems. Low solution $M_v$ with efficient grafting may also be achieved in the presence of radical inhibitors and with certain monomers.

e) Degassing: Removal of oxygen from the graft solutions by vacuum and/or inert gas (e.g., argon purging) has an important effect: lower total dose is required (practical grafting at less than 0.1 Mrad). Oxygen degassing also has a large effect on polymer $M_w$ and % conversion of monomer.

f) Free-Radical Scavengers: Free radical traps, usually reducing agents such as $Cu^+$, $Fe^{+2}$, ascorbic acid, etc., are known to inhibit radical polymerization in solution and thus be effective (especially at high gamma dose, high-dose rates and high monomer concentrations) in slowing the onset of solution gelation during grafting.

g) Swelling Solvents and Monomer Presoaking: The use of polymer substrate solvents in aqueous monomer grafting solutions facilitates swelling and monomer diffusion into the polymer before and during gamma polymerization. Penetration of monomers into the substrate increases graft coating thickness and enhances bonding to the surface. Prolonged exposure of polymeric substrates to monomers or monomer solutions is especially effective to promote such monomer diffusion prior to gamma grafting. For example, where an ocular implant surface is polymethylmethacrylate (PMMA), polypropylene (PP), polyvinylidene fluoride (PVDF), a polycarbonate (PC), a poly-siloxane (PSi), the surface is beneficially pre-soaked in monomer or a first aqueous solution containing from about 5 to about 95%, by weight, of the monomer, preferably at a temperature of from about 5° C. to about 90° C. and for a time period of from about 0.5 to about 48 hours or more, as described in copending application Ser. Nos. 07/592,478, now U.S. Pat. No. 5,108,776, and 07/592,484, now U.S. Pat. No. 5,094,876, both filed on Oct. 5, 1990, the entire disclosures of which are incorporated herein by reference.

N-vinylpyrrolidone (NVP), hydroxyethylmethacrylate (HEMA), vinyl substituted polyethers such as vinyl-polyethylene glycol (VPEG) or vinyl-polypropylene glycol (VPPG), acrylamide (AM), dimethylacrylamide (DMA), hydroxy-propylacrylates and other reactive hydrophilic monomers are also useful for gamma radiation grafting according to the process of this invention.

Where mixtures of NVP and HEMA are employed to form graft copolymerized coatings of P(NVP-HEMA), the mixtures may contain up to about 50% by weight of HEMA, based on the weight of the monomer mixture. However, above 20–30% HEMA, radical scavengers and low monomer concentrations are preferably used to prevent gelation since HEMA enhances the onset of gelation.

Any ethylenically unsaturated monomer capable of forming a graft polymerized coating, preferably hydrophilic, on the surfaces described herein when irradiated with gamma radiation or electron beam radiation under the conditions described herein may be employed in the practice of the invention.

It will be understood by those skilled in the art that the hydrophilic monomers may be copolymerized with other monomers including ionic monomers. Mixtures of hydrophilic and ionic monomers may also be copolymerized therewith. For example, graft copolymerization incorporating vinylsulfonic acids or vinylcarboxylic acids such as acrylic acid, crotonic acid or methacrylic acid can afford surface modifications which are anionic. Similarly, graft copolymerization incorporating amino-functional monomers, e.g., vinyl-pyridines, aminostyrenes or aminoacrylates, or aminomethacrylates such as dimethylaminoethylmethacrylate, or dimethylaminostyrenes afford surface modifications which are cationic.

Amounts of ionic monomers up to about 50 wt. % of the total monomer weight may be employed, it being understood that the critical process parameters listed above may be maintained.

The method of the invention is applicable for the surface modification of medical instruments, devices, implants and contact lenses formed from a variety of plastic, ceramic or metallic materials.

It will be understood by those skilled in the art that any surface may be modified according to the method of the invention provided that, when exposed to GDP under the conditions described herein, activated surface species or sites such as ions or radicals are formed therein which will bond with the polymers and copolymers graft polymerized thereon under the gamma- or electron beam-irradiation conditions described herein. It will be further understood that, in some instances, the activated sites formed on the surface by GDP may be advantageously exposed to oxygen to form chemically reactive atomic or molecular species or sites therein, such as peroxy or hydroperoxy groups, suitable for covalent bonding and graft copolymerization under requisite gamma- or electron beam-irradiation conditions.

Any instrument, device, implant, etc., constructed of one or more plastic, ceramic or metallic material component may be surface modified according to the present invention to improve the tissue contacting characteristics of the surfaces thereof.

The hydrophilic graft polymer surface modifications of this invention are advantageous for intraocular lens implants (anterior chamber, posterior chamber or phakic) but are also of great value in affording improved tissue protection and improved biocompatibility for other ocular implants such as corneal inlays, keratoprostheses, epikeratophalia devices, glaucoma shunts, retinal staples, scleral buckles, etc.

Plastic surgical instruments and implements such as probes, retractors, tissue and vessel separators, irrigation and aspiration tools, phacoemulsification tools, sponges, clamps, gloves, lens glides, positioning tools, forceps, insertion tools, staples, sutures, etc., may be treated to afford tissue-protective surface qualities in accordance with the present invention.

Medical devices such as hard and soft contact lenses, intravenous and central venous catheters, laser and balloon angioplasty devices, vascular and heart devices (tubes, catheters, balloons), ventricular assists, blood dialysis components, blood oxygenators, ureteral/urinary devices (Foley catheters, stents, tubes and balloons), airway catheters (endotracheal and tracheostomy tubes and cuffs), enteral feeding tubes, wound drainage tubes, blood bags and blood tubing may also be beneficially treated in accordance with the method of the present invention.

Implants which may be modified according to the present invention include, for example, vascular grafts, soft and hard tissue prostheses (mammary, cranio/facial, tendons, joints), heart valves and artificial hearts.

Modification of these instruments, devices, implants, etc., improves the surfaces thereof so as to improve blood compatibility and reduce tissue adhesion and tissue damage during surgical contact and manipulation. Moreover, the invention operates to reduce cell adhesion for reduced inflammation, reduce fibrous capsule formation for soft tissue implants, and reduce thrombogenicity for cardio-vascular devices and prostheses. The invention also acts to reduce bacterial adhesion and thereby reduce the incidence of infection and further operates to reduce interfacial abrasion and friction which is of special value for joint and tendon prostheses.

Polyolefins and polyolefin/hydrocarbon block polymers are useful for constructing medical tubing, catheters, blood bags, sutures, etc. Copolymers of the SBS, EP, or SE/BS type may be thermoplastic elastomers which combine rubbery properties with extrudable or injection moldable processing properties. Surface modification of such materials according to the present invention is effective in changing the normal surface characteristics of these polymers from hydrophobic to hydrophilic.

The fluorocarbon polymers are widely used for catheters (i.e., intravenous catheters), for vascular prostheses (i.e., vascular grafts) and for coating medical devices, instruments and implants due to their biocompatibility and inertness. However, the surface properties may be improved significantly according to the present invention to reduce cell and tissue adhesion and improve blood compatibility.

The silicone polymers are widely used for medical tubing and catheters, for mammary implants and other soft tissue prostheses. Hydrophilic surface modification, according to this invention, acts to reduce cell and tissue abrasion and adhesion and to thereby reduce fibrous capsule formation which is a major complication of soft tissue implants. Similarly, polyvinylchloride surface modification to produce more hydrophilic vinyl tubing and film surfaces can reduce thrombogenicity and improve biocompatibility of blood tubing, blood bags, catheters and other medical devices made of polyvinylchloride.

Polyurethanes which are used for such applications as pacer leads, intravenous catheters, enteral feeding tubes, vascular grafts, etc., are also beneficially modified by the process and materials of this invention to produce more hydrophilic surfaces and make such devices more biocompatible.

Each of the above-described process conditions and parameters of the method of the invention may be varied within the ranges discussed to produce certain specific combinations which are particularly advantageous for the surface modification of particular materials or combinations of materials.

The combined plasma-gamma surface modification process and coatings of this invention are uniquely applicable to metallic, ceramic or glass instruments or devices which are less readily chemically surface grafted than polymeric substrates.

Several ranges of process conditions appear useful. Choice of the "best" process will depend on such factors as molecular structure of substrate and coating thickness desired. In general, those gamma grafting conditions which may produce extreme solution viscosities or gels or conditions which could produce stress cracking or crazing of the surface should be avoided.

All percentages expressed in the examples are by weight unless otherwise stated.

It will be understood by those skilled in the art that the present invention is applicable to the treatment of any surface capable of oxidation or activation by GDP and formation of reactive sites due to the GDP and/or exposure of the activated surface to oxygen. Thus, the method is applicable to metallic, polymeric or ceramic materials.

Typical metallic surfaces which may be treated according to the method of the invention include iron and iron alloys including various alloy steels, nickel, copper, cobalt, tantalum and a wide variety of metallic alloys.

Suitable polymeric substrates include polyacrylates and -methacrylates (i.e., polymethylmethacrylate, polyethylacrylate, polybutylmethacrylate, etc.); polyolefins (polyethylene, polypropylene, polybutadiene); SBS copolymers (styrene-butadiene); ethylene-propylene copolymers; SE/BS (styrene-ethylene/butadiene-styrene) block copolymers; polycarbonates (PC); fluorocarbon polymers (i.e., polyvinylidene fluoride-PVDF, polytetrafluoroethylene-PTFE, polyperfluoroethylene-propylene-FEP); polysiloxanes; various aliphatic and aromatic polyurethanes, including polyurethane polyester or polyether block copolymers; polyvinylchloride; various polyesters including polyethylene terephthalate (PET); polycarbonate/polydimethylsiloxane copolymers (PC/PDMSO), etc.

Inorganic glasses and ceramics of various compositions such as silica, soda glass, borosilicate glass, high calcium and phosphate glasses, quartz, etc., may be utilized according to the present invention.

The invention is particularly adapted for the construction of polymeric, ceramic or metallic biomedical articles and articles which comprise two or more such materials such as surgical instruments and implements such as probes, retractors, tissue and vessel separators, irrigation and aspiration tools, phacoemulsification tools, sponges, clamps, gloves, lens glides, positioning tools, forceps, insertion tools, staples, sutures, etc., all of which may be treated in accordance with the present invention.

Medical devices such as hard and soft contact lenses, intravenous and central venous catheters, laser and balloon angioplasty devices, vascular and heart devices (tubes, catheters, balloons), ventricular assists, blood dialysis components, blood oxygenators, ureteral/urinary devices (Foley catheters, stents, tubes and balloons), airway catheters (endotracheal and tracheostomy tubes and cuffs) enteral feeding tubes, wound drainage tubes, blood bags and blood tubing may also be beneficially treated in accordance with the method of the present invention.

Implants which may be modified according to the present invention include, for example, intraocular lenses, vascular grafts, soft and hard tissue prostheses (mammary, cranio/facial, tendons, joints), heart valves and artificial hearts.

It will be further understood by those skilled in the art that the conditions employed in the GDP treatment such as that using RF-GDP will depend upon the particular surface being treated. Generally, however, exposure of the surface to RF-GDP at a power in the range of from about 1 to about 500 W or more for a time period of from about 1 sec. to about 30 min. will usually be sufficient to activate or oxidize the surface.

Figure 12:
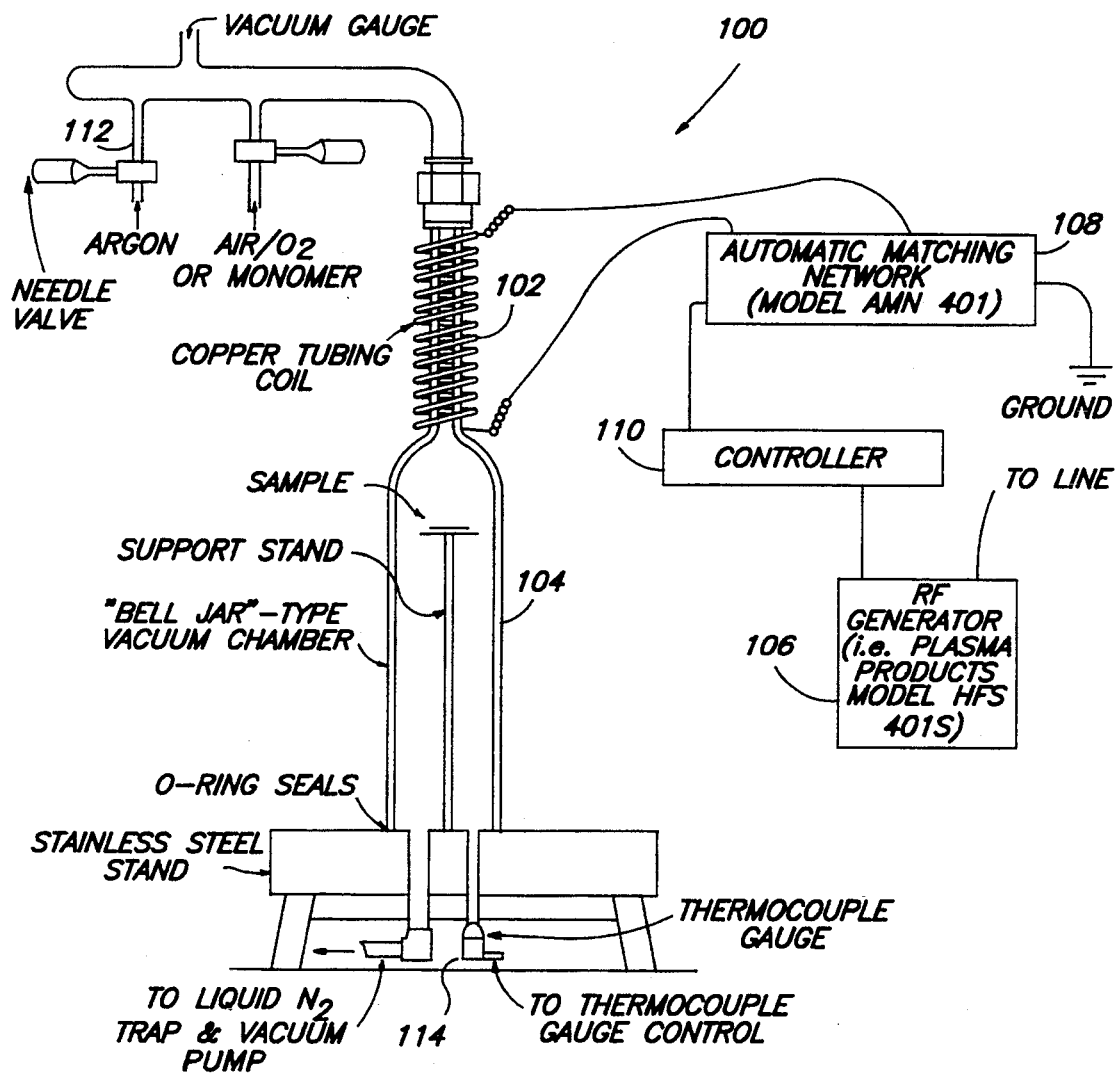
FIG. 12 represents a schematic diagram of an RF plasma generating apparatus.

Any conventional GDP generating system such as radio frequency (RF), microwave, or DC discharge system may be used in the practice of the invention. RF-GDP is used to illustrate one preferred embodiment of the practice of this invention for GDP activation of metal, ceramic or polymer surfaces prior to gamma radiation graft polymerization. RF-GDP treatments are typically carried out in a system such as that schematically represented in FIG. 12 by reference numeral 100. A copper coil 102 is wound around a portion of the pyrex vacuum chamber reactor 104 to excite a GDP. The system illustrated used a 13.56 MHz RF generator 106 (model HFS 40155, RF Plasma Products, Inc.) rated to 500 W. The coil and generator are matched using a matching network 108 (Model AMN-502, RF Plasma Products, Inc.) and controller 110. The system is typically evacuated to $10^{-4}$ Torr or less via a vacuum pump (not shown) and the glow discharge established with argon (or any other suitable gas) introduced via inlet 112 increasing the pressure to about 0.2 Torr. Time (seconds to minutes) and power (1 to 500 W) are readily varied. The temperature of the system is monitored by thermocouple 114.

Exposure of the activated surface to oxygen, air or water vapor can result in the formation of surface peroxy and/or hydroperoxy groups to facilitate subsequent graft polymerization.

The invention is illustrated by the following non-limiting examples.

EXAMPLE 1

This example illustrates the RF-GDP surface treatment of polymethylmethacrylate (PMMA), polydimethylsiloxane (PDMSO), biphenol polycarbonate (PC) and perfluoroethylene/propylene (FEP Teflon) and the subsequent gamma radiation graft polymerization of N-vinylpyrrolidone (NVP) and acrylamide (AM) on RF-GDP activated PMMA and PDMSO substrates to produce improved hydrophilic polymer graft surfaces.

The RF-GDP system containing the substrate was evacuated to about 20 microns and argon admitted to the system to initiate the GDP at about 200 microns. Plasma power was 10–50 W, substrates were exposed to the GDP for 10 seconds to 5 minutes and then to air with release of the vacuum. Results are summarized in Table 1 which shows the effect of power and time on hydrophilicity after exposure to air, which change in the surface properties is indicative of the GDP surface activation and modification due to the GDP exposure. Also shown is the behavior of the GDP treated surface after prolonged (48 hrs.) exposure to water. Using RF-GDP conditions of 50 W and 90 sec. exposure, PMMA and PDMSO substrates were RF-GDP treated and then gamma polymerization grafted using AM and NVP monomers.

TABLE 1

Effect of Plasma Power and Time on Substrate Hydrophilicity

| Sample | Plasma Power | Plasma Time | Air Bubble Contact Angle t = 0 | Air Bubble Contact Angle t = 48 hrs (in water) |
|---|---|---|---|---|
| FEP | — | — | 95 | 95 |
|  | 10 W | 10 sec | 54 | 70 |
|  | 25 | 2 min | 53 | 47 |
|  | 50 | 5 min | 54 | 40 |
| PC | — | — | 76 | 74 |
|  | 10 W | 10 sec | 21 | 46 |
|  | 25 | 2 min | 20 | 36 |
|  | 50 | 5 min | 25 | 32 |
| PMMA | — | — | 70 | 60 |
|  | 10 W | 10 sec | 33 | 37 |
|  | 25 | 2 min | 36 | 43 |
|  | 50 | 90 sec | 25 | 25 |
| PDMSO | — | — | 110 | 110 |
|  | 25 W | 2 min | 50 | 110 |
|  | 50 | 90 sec | 25 | 25 |

Figure 3:
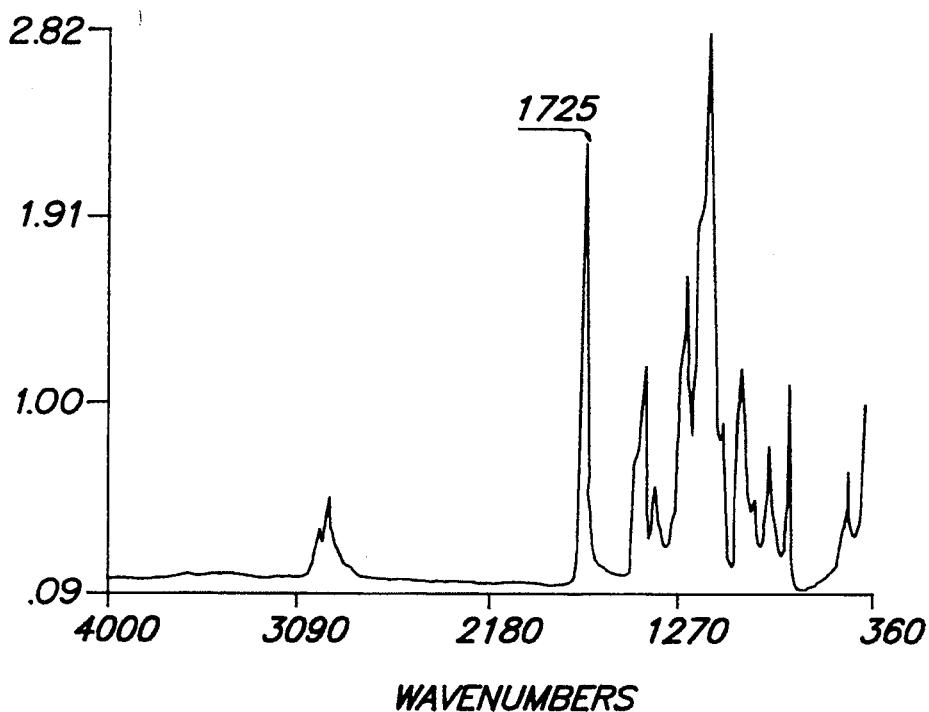
Figure 4:
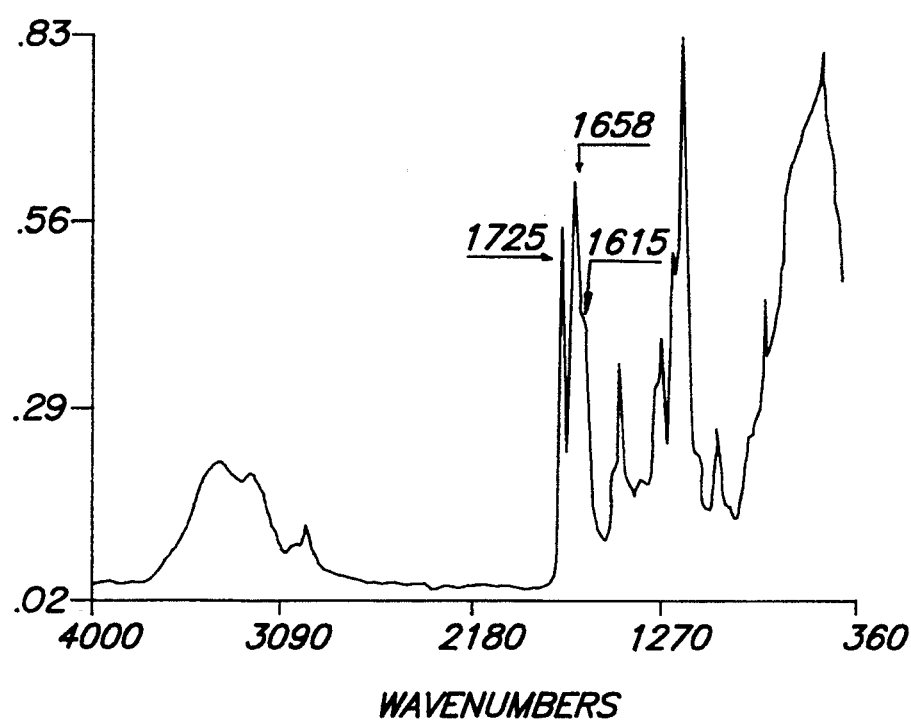

After plasma treatment, the substrates were exposed to air, placed in a 10% aqueous monomer solution, the system oxygen degassed by argon purge, and then irradiated in a Cobalt-60 source to a dose of about 0.01 Mrad. Samples were thoroughly washed with water to remove homopolymer and/or residual monomer. FIG. 3 is the FTIR/ATR spectrum for untreated PMMA. The spectrum of a typical graft of polyacrylamide (PAM) on PMMA PAM-g-PMMA is shown in FIG. 4. The strong absorption bands at 1658 and 1615 cm$^{-1}$ correspond respectively to the —C═O stretch and —N—H bending frequencies of the

Figure 5:
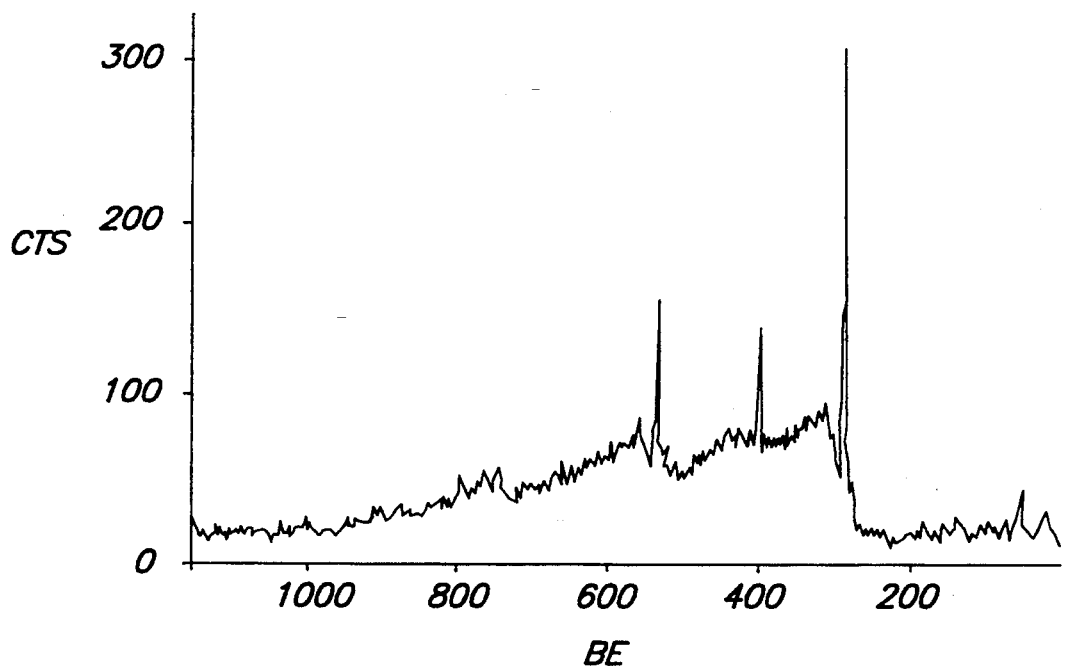

The X-ray photoelectron spectroscopy (XPS) spectrum of this sample (FIG. 5 and Table 2) shows an almost perfect match with the oxygen content (15.7%) and nitrogen content (13%) of PAM.

Figure 6:
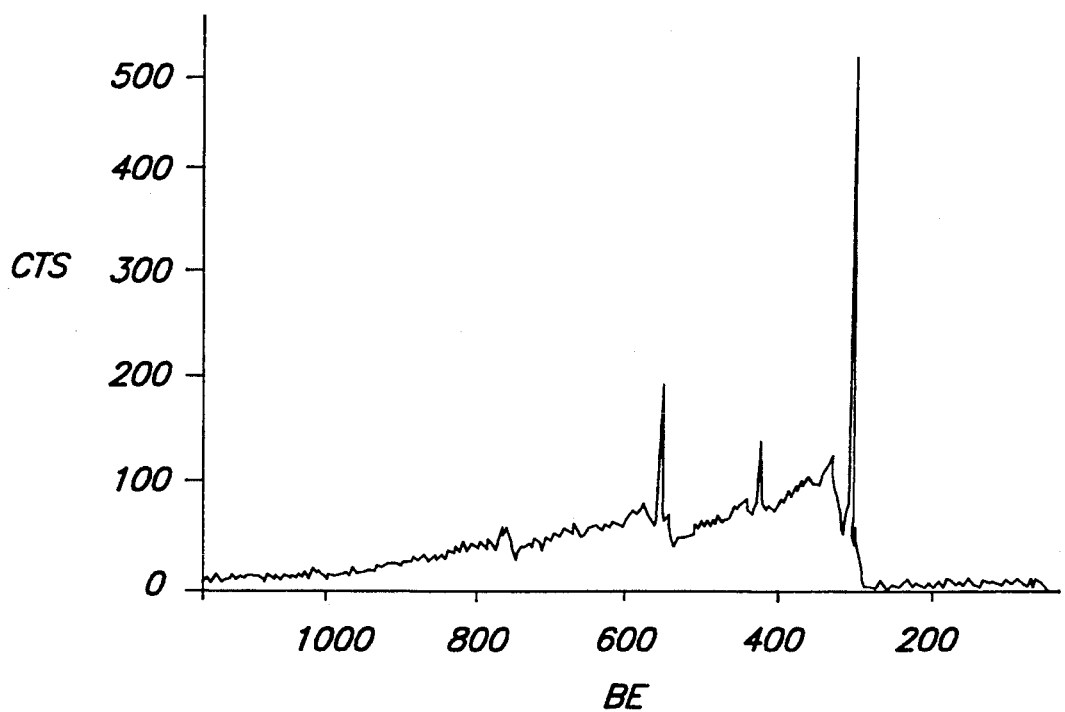
Figure 7:
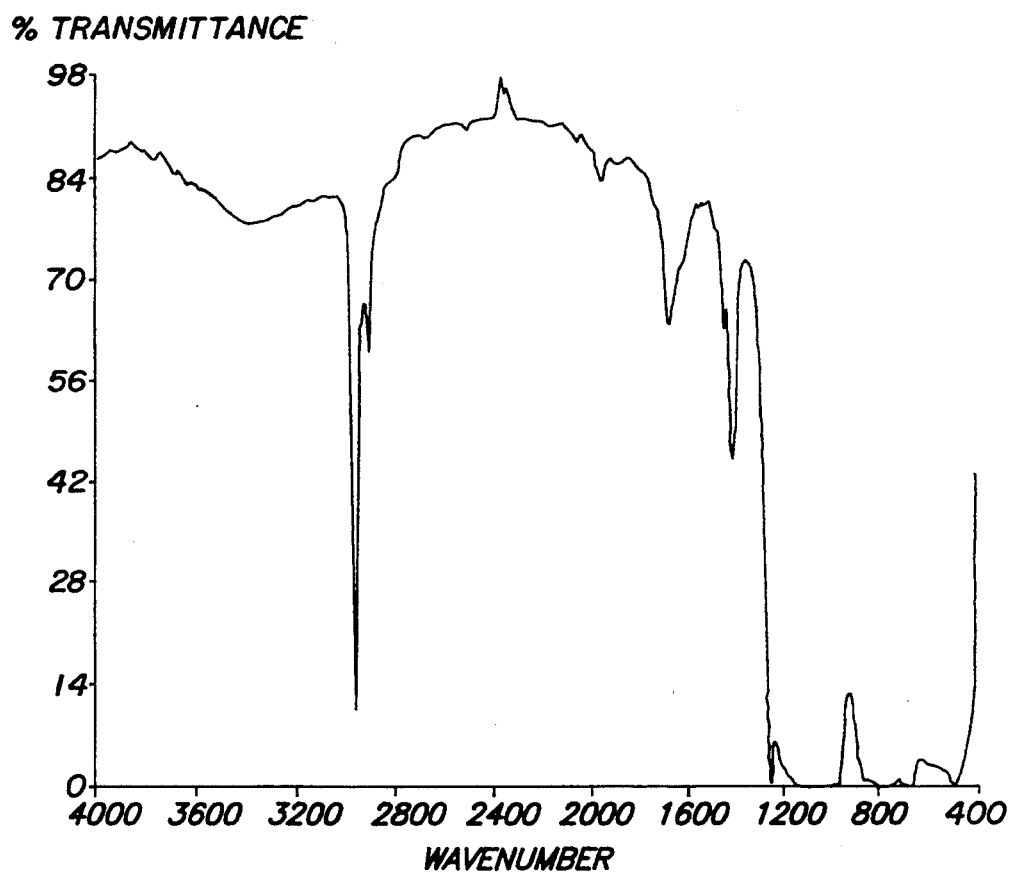
Figure 8:
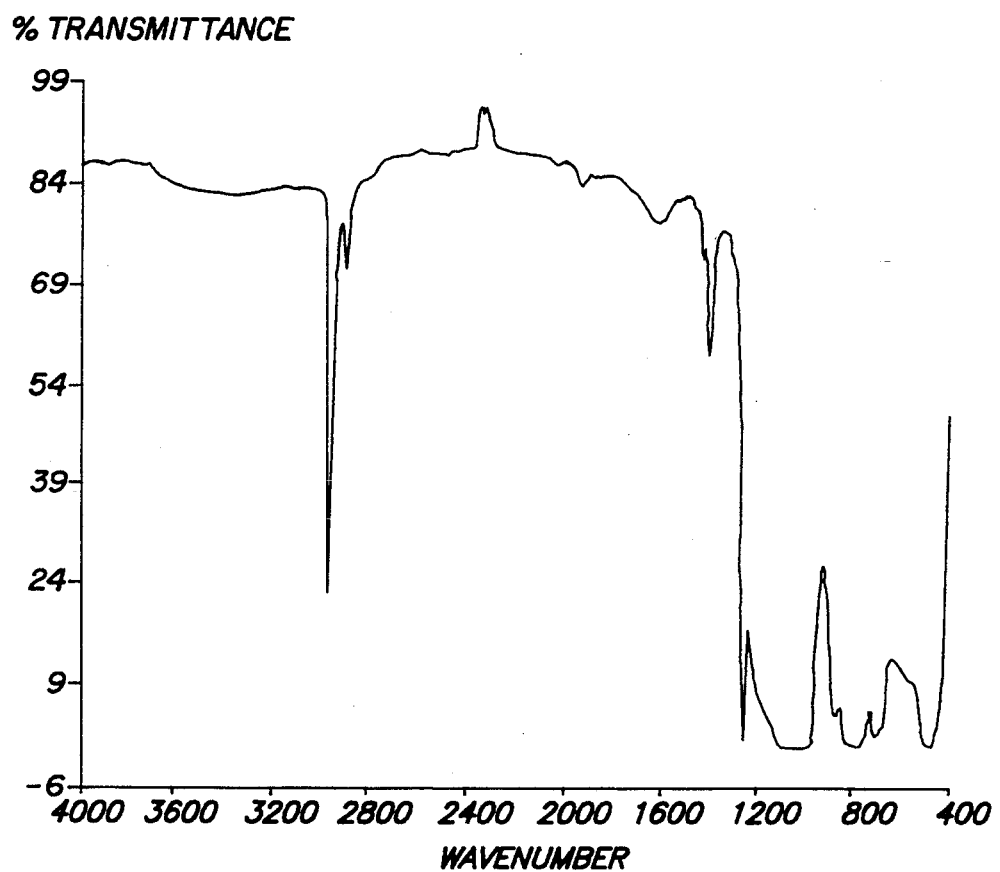
Figure 9:
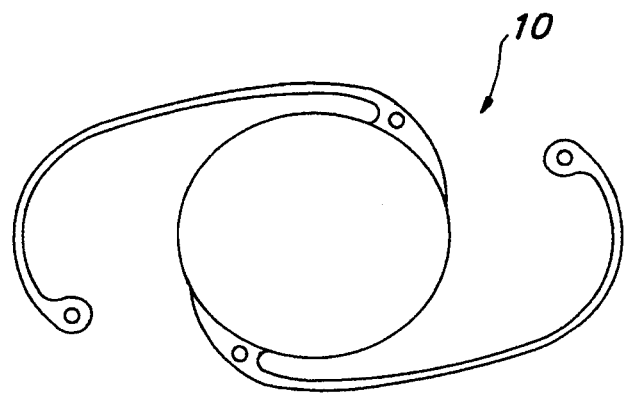
FIG. 9 depicts a top view of a one-piece intraocular lens 10 constructed of a material according to the present invention.
Figure 10:
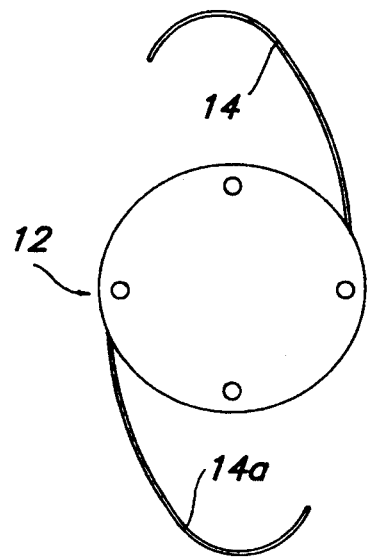
FIG. 10 depicts a top view of an intraocular lens 12 with fiber haptics 14 which may be made of a different substrate polymer than the optic and constructed of a material according to the present invention.
Figure 11:
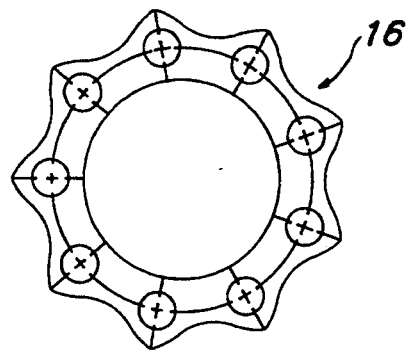
FIG. 11 depicts a top view of a keratoprosthesis 16 constructed of a material according to the present invention.

Similar highly efficient grafting was obtained with NVP at 0.01 Mrad (FIG. 6). FIGS. 7 and 8 show the FTIR/ATR spectra for PAM-g-PDMSO and PVP-g-PDMSO, respectively. In both cases, it can be seen that good grafting is obtained. The relative intensities of the carbonyl peaks suggest that somewhat more efficient grafting is obtained with AM perhaps due to the greater reactivity of AM as compared with NVP. Similar behavior was noticed for grafting on PMMA.

Figure 2:
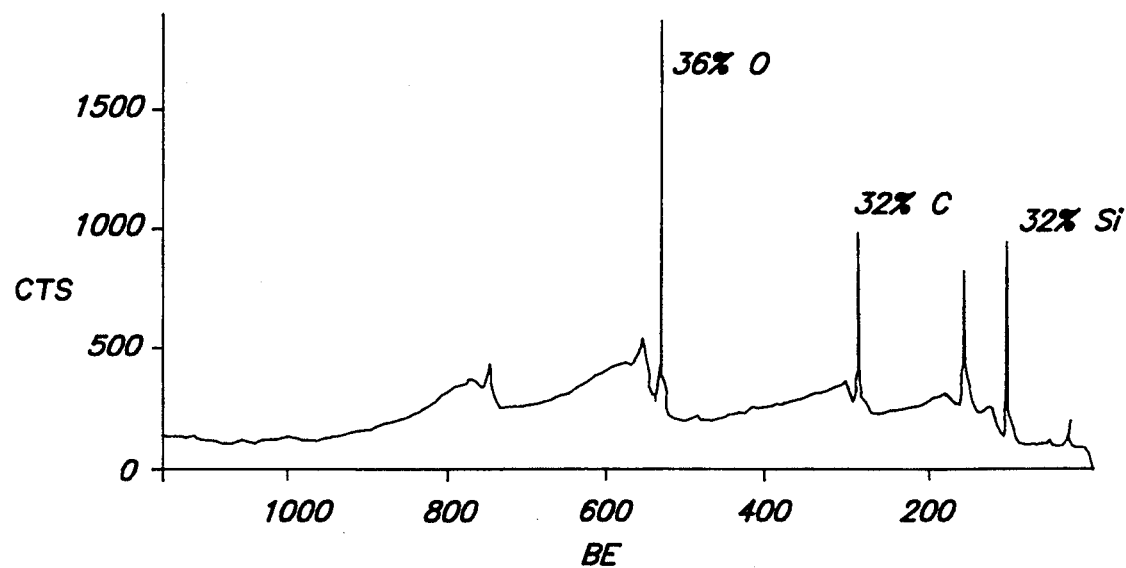
FIGS. 2, 3, 4, 5, 6, 7 and 8 are spectral analyses of surfaces of a variety of materials treated in accordance with the method of the present invention, as well as comparisons thereof with other surfaces.

FIGS. 1 and 2 depict the XPS spectra for untreated PDMSO and argon plasma treated PDMSO, respectively.

To show the great improvement in grafting efficiency, control experiments were conducted with PMMA and PDMSO substrates without initial RF-GDP activation, but using the same gamma radiation graft conditions. These control samples showed much less evidence of grafting as indicated by FTIR/ATR and XPS analyses.

TABLE 2

XPS Analyses for PAM and PVP Grafts On PMMA and PDMSO Using GDP/Gamma Grafting*

| Sample | % C | % O | % N | % Si |
|---|---|---|---|---|
| PAM-g-PMMA | 71.3 | 15.7 | 13.0 | — |
| PVP-g-PMMA | 79.6 | 13.5 | 6.9 | — |
| PAM-g-PDMSO | 64.9 | 16.6 | 7.5 | 11.0 |
| PVP-g-PDMSO | 52.3 | 24.1 | 4.0 | 19.5 |
| PMMA (Exp.) | 77.8 | 22.2 | — | — |
| PDMSO (Exp.) | 48.0 | 23.0 | — | 29.0 |

*Graft Conditions: Plasma 50 W, 90 sec., 100 microns, Argon; Gamma 10% NVP, 0.01 Mrad, 266 rads/min.

EXAMPLE 2

This example demonstrates the highly efficient surface graft achieved with NVP on various substrates by the above-described plasma/gamma surface modification process. Table 3 gives contact angle measurements for three hydrophobic polymers which are relatively inert chemically and therefor difficult to gamma graft and for stainless steel and glass. The plasma/gamma graft process was as described in Example 1. Comparisons are made with control substrates and with substrates irradiated at 93 rad/min. to 0.01 Mrad in 10% aqueous NVP. Contact angles were significantly decreased for all substrates using the plasma/gamma process, indicating efficient PVP grafting. Without GDP pretreatment, there was no significant change in the contact angle of FEP Teflon, PDMSO, stainless steel or glass. PVDF also showed an improvement in hydrophilicity using plasma/gamma grafting, but to a somewhat lesser degree. These data show that the plasma/gamma process is a very significant improvement and particularly advantageous for surface grafting of chemically stable, gamma graft resistant polymeric, metallic and glass substrates.

TABLE 3

Contact Angle Measurements For PVP Grafted Substrates Showing Improvement Using Plasma/Gamma Process

| Sample | Untreated Control | Contact Angle | |
|---|---|---|---|
| | | Gamma[1] | Plasma/Gamma[2] |
| FEP | 95° | 95° | 19° |
| PDMSO | 110° | 110° | 25° |
| PVDF | 75° | 29° | 18° |
| S.S.[3] | 45° | 45° | 36° |

TABLE 3-continued

Contact Angle Measurements For PVP Grafted Substrates Showing Improvement Using Plasma/Gamma Process

| Sample | Untreated Control | Contact Angle | |
|---|---|---|---|
| | | Gamma[1] | Plasma/Gamma[2] |
| S.S.[4] | 45° | 44° | 21° |
| Glass[5] | 40° | 43° | 16° |

[1] 93 rad/min., 0.01 Mrad, 10% NVP
[2] 25 W, 2 min., Argon, 93 rad/min., 0.01 Mrad, 10% NVP
[3] S.S. = 316 Stainless steel
[4] S.S. using 50 W and 5 min. for RF-GDP conditions
[5] Microscope Slide

EXAMPLE 3

The effect of plasma gas (argon or $O_2$) on plasma/gamma PVP grafting of FEP and PP was also examined (Table 4) with little apparent difference between the argon plasma or $O_2$ containing plasma. Two gamma dose rates were also compared. The higher dose rate is less efficient for gamma grafting alone and demonstrates the improvement resulting from plasma pretreatment yielding 14°–18° C.A. for the plasma/gamma process for PP compared to 30°–41° using only gamma grafting under these conditions.

TABLE 4

Effect of Plasma Gas on Plasma/Gamma Grafting of PVP on FEP and Polypropylene

| Sample/Conditions | | C.A.° |
|---|---|---|
| (25 W/2 min.: 93 rads/min., 0.01 Mrad, 10% NVP) | | |
| FEP: | RF/$O_2$ | 20 |
| FEP: | RF/Ar | 19 |
| FEP: | (93 rads/min., 0.01 Mrad, 10% NVP) No Plasma | 95 |
| (25 W/2 min.: 93 rads/min., 0.01 Mrad, 10% NVP) | | |
| PP: | RF/$O_2$ | 20 |
| PP: | RF/Ar | 20 |
| PP: | (1065 rads/min., 0.01 Mrad, 10% NVP) No Plasma | 41 |
| (25 W/2 min.: 93 rads/min., 0.01 Mrad, 10% NVP) | | |
| PP: | RP/$O_2$ | 14 |
| PP: | RF/Ar | 18 |
| PP: | (93 rads/min., 0.01 Mrad, 10% NVP) No Plasma | 30 |

EXAMPLE 4

The plasma/gamma process of this invention is uniquely effective for polymer surface modification of metal substrates and, therefore, of particular value for altering the surfaces of metallic medical instruments and devices, metallic electronic devices, etc. Depending upon surface chemical stability, metals may require higher plasma power (to 500 W or more) or prolonged plasma treatment time (30–60 min. or more). This example demonstrates the effect of RF-GDP conditions on PVP grafting of stainless steel. Gamma grafting alone effects no significant change in surface hydrophilicity for stainless steel. However, the plasma/gamma graft process effects a significant reduction in contact angle and produces a highly hydrophilic surface modification.

Surgical steel instruments such as clamps, retractors and forceps are readily surface modified with hydrophilic graft polymers by the combined plasma/gamma process of this invention to yield surfaces which are less traumatic in contact with fragile tissues (i.e., ocular, peritoneal, pericardial, fallopian tube, etc.) and also less damaging to implants (i.e., intraocular, vascular, mammary, etc.) during surgical manipulation. For example, a steel forcep is PVP surface modified by the combined plasma/gamma process under conditions of 150 W/2 min. argon plasma treatment followed by gamma PVP grafting at 93 rads/min. to 0.01 Mrad in 10% aqueous NVP. The resulting hydrophilic surface modification is more gentle in contact with tissues and produces less surgical trauma during surgical manipulations. A steel intraocular lens positioning tool is surface modified under these conditions to yield an instrument which is less damaging to contacted ocular tissues and less damaging to plastic lens implant surfaces which are manipulated.

TABLE 5

Effect of Plasma Conditions on Plasma/Gamma Grafting of Stainless Steel with PVP

| Sample/Conditions | Contact Angle |
| --- | --- |
| Stainless Steel (SS) | 45° |
| SS - Gamma Graft Only 93 rads/min., 0.1 Mrad, 10% NVP | 44° |
| 25 W/2 min.: 93 rads/min., 0.01 Mrad, 10% NVP | 36° |
| 50 W/5 min.: 0.01 Mrad, 10% NVP | 21° |
| 150 W/2 min.: 0.01 Mrad, 10% NVP | 17° |

The following are examples of hydrophilic polymer surface modifications of devices and instruments by gamma polymerization grafting of various monomers on various substrates. All examples show significantly improved surface modification by employing the plasma/gamma process of this invention instead of gamma grafting alone. Much milder gamma graft conditions (as low as 0.001–0.01 Mrad or less) and improved graft efficiency are achieved for the following gamma grafts by the combined use of GDP treatment and gamma radiation grafting.

EXAMPLE 5

Hydrophilic Surface Modification of FEP Teflon Intravenous Catheter Polymers by $\gamma$-PVP and $\gamma$-PVP/HEMA FEP Teflon is a fluorocarbon polymer which is used for a number of medical devices such as intravenous catheters. It is very hydrophobic with a contact angle greater than 95° and shows significant tissue adhesion and damage on contact as indicated by in vitro rabbit corneal endothelium tests: about 250 mg/cm$^2$ adhesion force and 30–50% cells destroyed. FEP Teflon film was surface modified by the following procedure to produce hydrophilic surfaces with contact angles less than 30°–40°, with tissue adhesion reduced to less than about 120 mg/cm$^2$, and tissue damage reduced to less than 20%. For example, FEP films immersed in 25% aqueous NVP monomer and irradiated to gamma doses of 0.10 and 0.25 Mrad (without oxygen degassing) yield hydrophilic PVP graft surfaces with contact angles of 33° and 26°, respectively. The endothelium adhesion force was 45 mg/cm$^2$ for the latter sample and FTIR-/ATR spectroscopy verified the presence of the PVP surface graft. The combined plasma/gamma process requires much lower doses, shorter times and is more efficient. FEP intravenous catheters exhibit improved surface properties when hydrophilic surface modified by the materials and processes of this invention; i.e., reduced pain and insertion force, reduced vascular endothelium damage, improved blood compatibility and reduced susceptibility to adherence of pathogens and associated infections. Central venous catheters and heart catheters are also beneficially surface modified in this manner. Other fluorocarbon polymer catheters (e.g., PTFE) are similarly improved by this hydrophilic surface modification.

EXAMPLE 6

Hydrophilic Surface Modification of Porous PTFE Vascular Graft (Goretex TM by $\gamma$-PVP Process Porous PTFE vascular grafts are presoaked in acetone, acetone-water-monomer solutions and then irradiated immersed in an aqueous monomer solution; typically 10% NVP, 5% acetone, 85% water in a gamma source to 0.02–0.15 Mrad total dose. After thorough washing with water, the PTFE was characterized and shown to have a hydrophilic surface modification by a major reduction in contact angle (from 98° unmodified to about 20° for the PVP surface graft). The PVP surface modification is also shown by FTIR/ATR surface spectroscopy. The mechanical properties of the fluorocarbon polymer substrate are virtually unchanged by the very low gamma radiation doses required for hydrophilic polymer grafting. The surface modification is shown to have little effect upon the porous structure of the PTFE vascular graft by scanning electron microscopy.

The resulting hydrophilic surface modified PTFE and porous vascular graft materials exhibit improved blood compatibility properties of special value for small diameter vascular grafts and for other blood contacting implants and devices, i.e., heart valves, ventricular assists, artificial hearts, vascular catheters and pacer leads.

EXAMPLE 7

NVP-HEMA Copolymer Gamma Grafting On FEP Teflon I.V. Catheters

NVP-HEMA copolymer gamma-grafting of FEP Teflon was found to be efficient at NVP:HEMA ratios of 9:1 and 8:2 yielding hydrophilic surface modification with 10% aqueous monomer solutions and 0.1 Mrad (contact angles of 30° or less). At 8:2 NVP-HEMA and 10% monomer, contact angles less than 30° can be achieved at 0.05 Mrad. Hydrophilic surface modified FEP Teflon intravenous catheters are readily prepared by this method to yield catheters with reduced insertion force and pain, and which are less likely to exhibit I.V. catheter complications such as infection, phlebitis, clotting, etc.

EXAMPLE 8

Surface Modification of Polyurethanes

Polyurethanes (PUR) have become increasingly important polymers for medical devices and implants, especially for I.V. catheters, pacer leads, vascular grafts and artificial heart applications. Although PURs are generally more hydrophilic than silicones or fluorocarbons, they do not generally exhibit the significant reduction in tissue adhesion and low tissue damage properties of more hydrophilic graft polymer surface modifications, i.e., PVP gamma grafts. Improved surface properties for medical devices and implants are achieved by the gamma-irradiation surface modification process of this invention.

For example, films of a 55 durometer polyurethane polyether block copolymer (Pellthane 5363) were gamma irradiated to 0.1 Mrad in oxygen degassed 10% aqueous NVP to yield significantly more hydrophilic surfaces. The unmodified contact angle of 54° was reduced to 28° for the PVP surface modified PUR. In vitro endothelium contact damage tests for PURs yield cell damage results averaging 60% or more compared to cell damage of less than 20% which is found for the hydrophilic PVP surface modifications. This improvement in PUR surface properties is especially important for commonly used radio-opaque PUR formulations containing such additives as barium sulfate because such formulations tend to have poorer biocompatibility. A typical PUR (Pellthane) formulation containing about 12% $BaSO_4$, for example, exhibits very high endothelium contact damage (80%) which is greatly reduced (<30%) by hydrophilic polymer surface modification.

TABLE 6

Tissue Damage Data Using In Vitro Rabbit Endothelium Contact Testing For Different Polymers Compared to Hydrophilic PVP Grafts

| | Contact Angle | % Endothelial Cell Damage |
|---|---|---|
| PMMA | 65-72° | 60-80% |
| FEP Fluorocarbon | 95-105° | 30-50% |
| Silicone | 90-100° | 60-80% |
| Gamma-PVP on PMMA | | <20% |
| Gamma-PVP on Silicone | | <20% |
| Gamma-PVP on FEP fluorocarbon | | <20% |

It is conventional for many medical device polymers to be filled with barium or bismuth radio-opaque compounds (i.e., $BaSO_4$) to enable X-ray examination. This can make surfaces even more damaging to tissues. Surface modification according to the method of the present invention is especially beneficial for such radio-opaque polymer compositions to provide smoother, tissue-protective, more biocompatible surface.

EXAMPLE 9

Hydrophilic Surface Modified PMMA Contact Lenses

This example illustrates the beneficial tissue-protective properties obtained by hydrophilic polymer surface modification of conventional hard (PMMA) contact lenses. Such contact lenses are normally irritating and abrasive to the external corneal epithelium. PMMA contact lenses are surface modified by gamma-graft polymerization immersed in aqueous NVP monomer (typically 10% NVP) using 0.1 Mrad dose. The resulting transparent hydrophilic graft makes the contact lens surface water wettable (30° C.A.) and non-adherent to the epithelial surface, thereby reducing epithelial abrasion and irritation. The various process improvements of this invention may be readily adapted to produce contact lenses with controlled surface modification thickness suited to specific patient needs.

EXAMPLE 10

Hydrophilic Surface Modified Silicone Soft Contact Lenses

Silicone soft contact lenses are widely used due to their mechanical flexibility and good oxygen permeability. However, silicone is normally hydrophobic. It is, therefore, not water wettable and may adhere to or abrade sensitive corneal epithelial tissue. Many types of silicone contact lenses are surface-treated with an oxidizing plasma to increase water wettability and minimize this problem. However, this type of surface oxidation has only a slight tissue-protective value and is usually transient in aqueous media. The silicone surface loses its hydrophilicity and becomes less wettable, often within a few weeks. In contrast, the hydrophilic polymer surface grafts of this invention are permanently bound chemically and persist indefinitely to maintain excellent water wettability. Furthermore, they exhibit non-adherent, lubricous, tissue-protective qualities in contact with the corneal epithelium, thereby minimizing abrasion and irritation while retaining the favorable optical, mechanical and oxygen permeability properties of the polysiloxane.

Commercially available silicone contact lenses are modified by gamma surface modification. Typically, silicone contact lenses are gamma-irradiated in 10% aqueous NVP-HEMA (10:1) to 0.1 Mrad to yield a hydrophilic surface modification with a C.A. less than 35° which is more stable in aqueous media and which is significantly less irritating to the corneal epithelium. Use of the plasma/gamma process of this invention yields more stable grafts under much milder graft process conditions.

EXAMPLE 11

Hydrophilic Surface Modified Endotracheal Tubes and Cuffs

Endotracheal and tracheostomy tubes are conventionally made of silicones, polyurethanes, fluorocarbon polymers and polyvinyl chlorides. Balloons or cuffs on these airway devices are inflated during intubation and are usually made of latex rubber, vinyl or silicone polymers. Significant clinical problems associated with the use of these devices are desquamation of the ciliated cells of the trachea and even more severe damage to the trachea due to the pressure, irritation and adhesion of the cuffs. Post-operative infections are associated with adherence of pathogens to the damaged and denuded areas of the trachea caused by the airway tube cuffs. Hydrophilic polymer surface modification of the tube and cuff surfaces according to this invention affords a significant improvement in these devices by minimizing abrasive contacts and adhesion to the sensitive tracheal tissues.

A silicone cuff is modified with PVP-PHEMA (10:1) by gamma grafting. The resulting hydrophilic cuff has markedly reduced adhesion to tissue and causes less tracheal irritation and damage than hydrophobic polysiloxane cuffs. Similarly, a latex rubber cuff is modified with gamma-grafted PVP. The resulting hydrophilic cuff is less adherent to sensitive tracheal tissue than normal hydrophobic latex rubber cuffs, causing less tracheal irritation and damage during intubation.

EXAMPLE 12

Hydrophilic Surface Modification of Foley Catheter Tubes and Balloons

Foley catheter tubes and balloons are used for catheterization of the urinary tract and conventionally made of the same hydrophobic polymers used for endotracheal tubes and cuffs as noted in Example 18. Clinical complications associated with such devices are tissue irritation, infection and encrustation due to the tissue adherent and damaging surface properties of the hydrophobic catheters and the adherence of pathogens, proteins and minerals to the surfaces. Although silicone and fluorocarbon polymers tend to exhibit reduced mineral deposits and encrustation, hydrophilic polymer surface modification affords improved resistance to the problems of tissue irritation, infection and encrustation.

A silicone Foley catheter is modified by gamma grafting with PVP-PHEMA (10:1). The resulting hydrophilic surface modified catheter has reduced tissue adhesion and exhibits less encrustation than unmodified silicone. In another example of the advantages of this invention, a Foley catheter with a latex balloon is surface modified according to the method of Example 8 yielding a hydrophilic surface which is less likely to promote infection and is less susceptible to encrustation.

EXAMPLE 13

Hydrophilic Surface Modification of Surgical Gloves and Sponges

Latex rubber surgical gloves exhibit hydrophobic surface properties and tend to adhere to sensitive tissue surfaces, thereby enhancing manipulative damage to tissues in all types of surgery. Manipulative damage can result in increased post-operative complications such as infection and surgical adhesions. Hydrophilic surface modification of surgical gloves results in reduced tissue adhesion of the rubber latex and less chance of severe manipulative tissue trauma due to contact with gloves. Latex rubber gloves are surface modified with a hydrophilic PVP gamma graft. The resulting hydrophilic latex surgical gloves are less adherent and less damaging to sensitive tissue normally contacted during surgery; i.e., peritoneum, pericardium, etc. The plasma/gamma process is particularly advantageous with latex because of the sensitivity of latex to degradation at higher gamma doses.

Surgical sponges and gauzes used in surgical procedures are also damaging to tissue due to tissue adhesion and abrasion. Sponges and gauzes are normally made of cotton, polyesters, cellulosic material and polyurethanes. These natural and synthetic polymers are all amenable to hydrophilic surface modification by the materials and processes of this invention. In a typical example, a cotton gauze sponge is surface modified by gamma-grafting with PVP using 10% aqueous NVP and 0.1 Mrad dose. The sponge surface is thereby rendered more hydrophilic and less abrasive to tissue during surgical manipulation without altering the structure and function of the sponge.

EXAMPLE 14

Hydrophilic Surface Modification of Silicone Mammary Prostheses

Mammary prostheses are most commonly constructed of a hydrophilic polysiloxane skin or membrane containing air, water or silicone gels or fluids. A major complication of such soft tissue prostheses is the irritation and inflammatory process which occurs at the tissue-implant interface which leads to formation of a hard fibrous capsule surrounding the implant. This fibrous capsule can severely compromise the bio-acceptance of the prothesis and, if severe, can lead to tissue necrosis, extrusion and loss of the implant. The hydrophilic surface modification of the silicone which is accomplished by this invention leads to reduced tissue irritation and abrasion by the implant and reduced adhesion of infiltrating cells during the postoperative period which normally can lead to extensive fibrous capsule formation. A silicone bag/silicone gel mammary prosthesis is surface modified with a hydrophilic PVP-PHEMA gamma graft at 0.1 Mrad. This hydrophilic prosthesis surface is less adherent to tissue or cells as compared to normal silicone and thereby has improved biocompatibility with less tendency to form a surrounding hard fibrous capsule. The plasma/gamma process improvement is particularly effective for polysiloxane surface modification in that the plasma treatment affects silicone surface changes which reduce molecular mobility and lead to more stable graft surfaces even using the very low gamma doses of 0.05 Mrad or less made possible by the plasma/gamma process.

EXAMPLE 15

Hydrophilic Surface Modification of Carbon Fiber Composite Reinforced Polycarbonate Surgical Instrument Plastic surgical instruments made of various hydrophobic structural polymers are used to an increasing extent because plastics lend themselves to high-quality, low-cost manufacture of special value for disposable instruments. Such instruments may exhibit significant tissue adhesion with accompanying manipulative trauma. Improved tissue-protective properties are achieved by the hydrophilic polymer surface modification of this invention. Fiber reinforced composites are among the most important examples of plastic materials used for instruments (containing glass, carbon or boron fibers to provide rigidity and high mechanical strength). A carbon fiber reinforced bisphenol-A polycarbonate microsurgical forcep for surgical insertion of an ocular implant is an example of a surgical instrument which is significantly improved by this invention. Using the gamma graft process, the carbon fiber reinforced polycarbonate instrument is readily surface modified with PVP. The resulting instrument surface is much less adherent to tissue and less damaging in contacts with fragile ocular tissues. Additionally, the surface modified plastic instrument is less likely to scratch or damage the surface of plastic ocular implants.

EXAMPLE 16

Hydrophilic Surface Modification of Silicone Irrigation/Aspiration (I/A) Tools Used In Ophthalmic Surgery In ophthalmic surgery, I/A tools are used to irrigate the eye with irrigating solutions and to aspirate fluids and tissue debris out of the eye. Silicone tips are commonly used on such I/A instruments. They are maneuvered around the anterior and posterior chambers of the eye with resulting frequent contacts with fragile tissues. For hydrophobic silicone devices, these tissue contacts may cause significant tissue damage which can compromise the success of the ocular surgery.

Silicone I/A tips are gamma graft surface modified with PVP and PVP-PHEMA. The resulting hydrophilic polymer surface is less adherent to tissue and less damaging on contact with sensitive tissues during surgery.

EXAMPLE 17

Hydrophilic Surface Modification of Polyurethane Artificial Heart

Implants or ex-vivo heart assist and artificial heart devices are most often constructed of woven fiber reinforced segmented polyether polyurethanes because of their superior mechanical strength properties. However, these materials are still thrombogenic to a significant degree and clotting complications severely limit the use of such devices. Modification of the surfaces of such devices with hydrophilic polymer grafts which are less thrombogenic by virtue of low blood cell and platelet adhesion and activation, low fibrinogen adsorption, etc., is efficacious in prolonging the useful life of such devices and implants. A polyurethane Jarvic-7-type artificial heart is readily surface modified with a PVP graft by the process of Example 15. This process is uniquely suitable for the uniform hydrophilic surface modification of highly irregular complex structures such as the artificial heart since the entire device is immersed in the monomer solution and radiation permeates the entire structure to uniformly activate the substrate and initiate surface graft polymerization in a controlled manner.

EXAMPLE 18

Hydrophilic Surface Modification Of Polyvinylchloride (PVC) Catheters

PVC is widely used for catheters, blood tubing, blood bags and many other medical devices. Formulations are hydrophobic and exhibit some adverse tissue adhesion and cell adhesion behavior. Hydrophilic surface modification is useful in improving blood and tissue compatibility. Since formulations often contain significant concentrations of plasticizers (i.e., dioctyl phthalate), leaching of surface plasticizer by washing with appropriate solvents such as aqueous acetone prior to gamma graft surface modification is preferred. After aqueous acetone washing, a PVC vascular catheter is exposed to 0.1 Mrad immersed in degassed 10% aqueous NVP to yield a hydrophilic PVP graft which exhibits less vascular endothelium damage on contact and which is less thrombogenic than unmodified PVC. The plasma/gamma process improvement is particularly effective for plasticized polymers of this type in that the initial plasma treatment effects surface changes which reduce molecular mobility and reduce plasticizer leaching. Plasticized polyvinylchloride blood bags, for example, are more efficiently surface modified with hydrophilic PVP, PHEMA or PVP-PHEMA by the process of this invention and thereby rendered more blood compatible and exhibit reduced permeability of potentially harmful plasticizers into the blood. Gamma graft efficiency is also enhanced such that gamma doses of 0.05 Mrad or less are effective.

EXAMPLE 19

Hydrophilic Grafting of Medical Devices Having Combinations of Materials

One of the important aspects of this invention is the discovery that certain grafting process conditions make it feasible to surface modify combinations of materials to be used in medical devices. Surface grafting of an assembled device can then take place in a one-step simultaneous grafting procedure yielding improved, more biocompatible surfaces. Material combinations of PMMA, PC, PUR, fluorocarbons, PP, PSi and other polymers can thereby be grafted under conditions of this invention. Table 7 lists some device material combinations with preferred mutual grafting conditions for obtaining gamma-PVP grafts which can be significantly improved using the plasma/gamma process of this invention.

PMMA/PP and PMMA/PVDF

It has been demonstrated that PMMA and PP gamma graft under degassed conditions at 157 rad/min., 0.05 Mrad, 10% NVP. These conditions yield contact angles of 20° and 15° for PMMA and PP, respectively, and are mechanically stable. Non-degassed PP does not graft efficiently under conditions similar to PMMA because of the adverse effect oxygen has on PP surface grafting.

PVDF surface graft studies also indicate the importance of oxygen degassing. A 10% degassed aqueous NVP solution, irradiated at 157 rad/min. to 0.05 Mrad, gives good hydrophilic grafts on both PMMA and PVDF. See Table 7.

PC/PP and PC/PVDF

PC and PP graft under similar gamma irradiation conditions when NVP solutions are degassed. Using 157 rad/min., 0.05 Mrad, and 10% aqueous NVP solutions, efficient hydrophilic grafting occurs on both polymers yielding contact angles of 19° and 15°, respectively.

PVDF and PC are both grafted under the same conditions which graft PC/PP and PMMA/PP combinations; e.g., 157 rad/min., 0.05 Mrad, 10% degassed NVP. Since PVDF swells in NVP, gamma grafting with prior swelling time can result in improved binding of P to the PVDF. Conditions are thereby afforded for simultaneous hydrophilic polymer grafting to devices which are made of two or more polymers as indicated above. See Table 7. In all cases, the combined plasma/gamma process greatly enhances the susceptibility of even difficult gamma graft substrates so that various combinations of materials, i.e., polymers or polymers with metals or ceramics, are greatly simplified.

TABLE 7

Gamma PVP Modification of Instruments and Devices Having Combinations of Materials

| Polymer Combination | Typical Preferred Gamma Polymerization Grafting Conditions* |
|---|---|
| PMMA/PP | a. 10% degassed NVP, low dose rate (LDR)**, 0.05 Mrad. |
| | b. 2.5% EtOAc, 6 hr swell, 10% NVP, degassed LDR, 0.05 Mrad. |
| PMMA/PVDF | a. 10% degassed NVP, LDR, 0.05 Mrad. |
| | b. 10% NVP, 5 hr swell, LDR, degassed, 0.15 Mrad. |
| | c. 2.4% EtOAc, 6 hr swell, 10% NVP, degassed, LDR, 0.05 Mrad. |
| PC/PP | a. 10% degassed NVP, LDR, 0.05 Mrad. |
| | b. 2.5% EtOAc. 6 hr swell, 10% NVP, LDR, degassed. |
| PC/PVDF | a. 10% degassed NVP, LDR, 0.05 Mrad. |
| | b. 10% NVP, 5 hr swell, LDR, degassed, 0.05 Mrad. |
| | c. 2.5% EtOAc, 6 hr swell, 10% NVP, degassed, LDR, 0.05 Mrad. |

*To produce C.A. less than about 25°.
**LDR: 30–300 rads/min.

EXAMPLE 20

This example illustrates the efficient grafting which can be achieved for the gamma or electron beam polymerization process of this invention at extremely low doses (0.005 Mrad or less) even at very low aqueous monomer concentrations (0.5 wt. % or less).

PVDF surfaces were surface modified using gamma radiation conditions described in previous examples at the extremely low gamma-radiation doses (0.01 and 0.005 Mrad) and low HEMA monomer concentrations (0.5–2.0%) summarized in Table 8. Highly hydrophilic surface graft modifications are achieved as indicated by the low contact angles listed in Table 8. Good grafting efficiency for PHEMA on PVDF under these extremely low dose and monomer concentration conditions was further confirmed by XPS analyses which showed little surface fluorine and a surface analysis which closely approximated the composition of PHEMA.

TABLE 8

Gamma Radiation Graft Polymerization of Argon Degassed Aqueous HEMA on PVDF at 88 rads/min.

| Total Dose (Mrads) | % HEMA | Contact Angle (°) |
|---|---|---|
| 0.005 | 0.5 | 24 |
|  | 1.0 | 24 |
|  | 2.0 | 12 |
| 0.01 | 0.5 | 21 |
|  | 1.0 | 19 |
|  | 2.0 | 16 |

Even at doses as low as 0.005 Mrad or less and monomer concentrations as low as 0.5 wt. % or less, extremely hydrophilic PHEMA grafts are obtained. For comparison, PVDF itself is very hydrophobic and has a contact angle greater than 85°.

EXAMPLE 21

The following demonstrates the enhancement of the above-described methods achieved by pre-soaking polymer substrate surfaces in a first solution of the monomer prior to graft polymerizing the monomer thereon from a second solution of the monomer.

The incorporation of monomer into the substrate by pre-soaking in monomer or aqueous monomer solutions at room temperature or elevated temperatures was found to be surprisingly simple and effective to facilitate the diffusion of monomer into the substrate to yield improved, thicker and more readily controlled grafted surface modifications. Practical conditions for this improved method are noted as follows by way of example:

Method A

Pre-soak in 100% NVP at 25° C. or 60° C. for 4–24 hours.
This method was used for PDMSO, PP, PVDF, polyethylene and polyurethane. However, it is not preferred for PMMA because of potential stress cracking and/or crazing of PMMA induced by 100% NVP.

Method B

Pre-soak in 40% aqueous NVP at 25° C. or 60° C. for 4–48 hours.
This method was used for substrates: PMMA, PDMSO, PP, PVDF, polyethylene, polyurethane and polyvinylchloride.

TABLE 9

Grafting of PVP on Various Substrates by Method A
Pre-soak in 100% NVP at 60° C. for 4 hours,
Grafting in 10% NVP with 0.15 Mrad at 484 rad/min.

| Substrate | % $W_m$ | % $W_g$ | % W, No Pre-soak | Air Bubble Contact Angle |
|---|---|---|---|---|
| PDMSO | 7.6 | 5.3 | 0.5 | 18° |
| PP (blue) | 5.7 | 3.9 | <0.1 | 18° |
| PP (clear) | — | 3.7 | — | 18° |

TABLE 9-continued

Grafting of PVP on Various Substrates by Method A
Pre-soak in 100% NVP at 60° C. for 4 hours,
Grafting in 10% NVP with 0.15 Mrad at 484 rad/min.

| Substrate | % $W_m$ | % $W_g$ | % W, No Pre-soak | Air Bubble Contact Angle |
|---|---|---|---|---|
| PVDF | 21.9 | 8.8 | 0.3 | 19° |

% $W_m$ = wt. % monomer uptake
% $W_g$ = wt. % graft

The above results show the improvement in gamma polymerization surface modification efficiency achieved by monomer pre-soaking just before gamma polymerization, i.e., increased weight gain for surface modification and highly hydrophilic surface.

Method C

Pre-soak in 100% DMAEMA, 100% NVP, 50% DMAEMA/50% NVP or 50% aqueous DMAEMA at 25° C. for 2–24 hours.
This method was useful for PDMSO, PMMA, PP and PVDF.

After pre-soak, samples (polymer slabs and lenses) were typically transferred to 10% aqueous NVP and vacuum or argon degassed. Gamma irradiation was carried out at room temperature in a Cobalt-60 source to a total dose of 0.15 Mrad. The dose rate used was 484 rad/min. Immediately after irradiation, samples were rinsed with warm water and then washed with repeated changes of distilled water for four days.

All bubble contact angles were measured under water to obtain wettability of the substrates and graft surfaces. Contact angles were usually measured for six bubbles, measured on both sides of a sample.

TABLE 10

Grafting of PVP on Various Substrates by Method B
Pre-soak in 40% NVP at 60° C. for 4 hours,
Grafting in 10% NVP with 0.15 Mrad at 484 rad/min.

| Substrate | % $W_m$ | % $W_g$ | % W, No Pre-soak | Air Bubble Contact Angle |
|---|---|---|---|---|
| PDMSO | 1.9 | 1.0 | 0.5 | 19° |
| PP (blue) | 0.8 | 0.5 | <0.1 | 18° |
| PP (clear) | — | 0.3 | — | 18° |
| PVDF | 5.9 | 5.1 | 0.3 | 18° |
| PMMA | 3.5 | 2.0 | 0.2 | 18° |

% $W_m$ = wt. % monomer uptake
% $W_g$ = wt. % graft

It can be seen from Tables 9 and 10 that monomer pre-soak before surface polymerization by gamma radiation enhances % $W_g$, the amount and efficiency of PVP grafting as compared with no monomer pre-soak.

TABLE 11

Effect of Pre-soak for PVP/SSA-g-PMMA
Varying Radiation Dose and Pre-soak Time

| Pre-soak (hrs.) | Grafting Dose (Mrad) | Air Bubble Contact Angle | % Graft (Gravimetric) |
|---|---|---|---|
| 0 | 0.1 | 50° | <0.1 |
| 0 | 0.2 | 48° | <0.1 |
| 6 | 0.2 | 21° | 0.2 |
| 12 | 0.2 | <10° | 0.1 |
| 12 | 0.15 | 11° | 0.2 |
| 24 | 0.15 | <10° | 0.3 |

As shown in Table 11, the pre-soaking with 30% NVP/SSA (2:1) comonomer solution just before gamma polymerization surface modification effects an increase in graft efficiency as indicated by the significantly increased hydrophilicity and the greater % grafting.

We claim:

1. A method for modifying a surface of a hydrophobic material by a gamma-irradiation or electron beam irradiation induced polymerization thereon of one or a mixture of ethylenically unsaturated monomers so as to form a hydrophilic polymeric coating on said surface, the improvement comprising the steps of:
   a) exposing said surface to a glow discharge plasma (GDP) having a power from about 1 to about 500 W and for a time sufficient to induce grafting sites on said surface for the surface graft polymerization of steps b and c;
   b) exposing said surface to a solution of an ethylenically unsaturated monomer or mixture thereof capable, via said ethylenic unsaturation, of gamma-irradiation or electron beam induced polymerization; and
   c) irradiating said activated surface with gamma or electron beam radiation in the presence of said ethylenic unsaturated monomer or mixture thereof to thereby form a hydrophilic polymeric surface coating on said surface, said polymerization being initiated by said gamma or electron beam radiation wherein said polymerization is conducted under the following conditions:
      i) monomer concentration in said solution in the range of from about 0.1% to about 50%, by weight;
      ii) total gamma or electron beam dose in the range of from about 0.001 to less than about 0.50 Mrad; and
      iii) gamma dose rate in the range of from about 10 to about 2500 rads/min, or electron beam dose rate in the range of from about 10 to about $10^8$ rads/min.

2. The method of claim 1, wherein said material is metallic, polymeric, ceramic, glass or quartz.

3. The method of claim 2, wherein said material is polymethylmethacrylate, polypropylene, polyvinylidene fluoride, polydimethylsiloxane, a polycarbonate, a polycarbonate/polydimethylsiloxane copolymer, polyethylene, polyvinylchloride, polytetrafluoroethylene, polyperfluoroethylenepropylene copolymers, polyurethanes, or polyurethane/polydimethylsiloxane copolymers.

4. The method of claim 2, wherein said material is iron, stainless steel, tantalum, titanium, aluminum, copper or chromium, or alloys thereof.

5. The method of claim 1, wherein said material is a biomedical article.

6. The method of claim 5, wherein said bio-medical article is a prosthetic implant or surgical instrument.

7. The method of claim 1, wherein said GDP is RF-, microwave- or DC discharge-generated.

8. The method of claim 1, wherein said surface is exposed to RF-GDP for a time in the range of from about 0.1 sec. to about 120 min.

9. The method of claim 1, wherein said GDP treated surface is exposed to air, water vapor or oxygen before said gamma-irradiation induced polymerization.

10. The method of claim 1, wherein said GDP treated surface is pre-soaked in one or more of said ethylenically unsaturated monomers or in a first aqueous solution of one or more monomers, having a concentration of monomer therein of from 5 to about 95% by weight, and conducting said gamma-irradiation or electron beam induced polymerization in a second aqueous solution of one or more of said monomers.

11. The method of claim 1, wherein said monomer is N-vinylpyrrolidone, hydroxyethylmethacrylate, acrylamide, dimethylacrylamide, diemthylaminoethylmethacrylate, acrylic acid, methacrylic acid, a vinyl substituted polyethylene or polypropylene glycol, a vinylpyridine, or a vinylsulfonic acid.

12. The method of claim 1, wherein said monomer or mixture of monomers is gamma-irradiation induced copolymerized with an ionic monomer or mixture thereof, the total monomer concentration in said solution being in the range of from about 0.1% to about 50%, by weight.

13. The method of claim 12, wherein said ionic monomer is a vinylsulfonic acid or a vinylcarboxylic acid.

14. The method of claim 13, wherein said vinylsulfonic acid is styrene sulfonic acid, vinylsulfonic acid, or a sulfoalkylacrylate.

15. The method of claim 13, wherein said vinyl-carboxylic acid is acrylic, methacrylic or crotonic acid.

16. The method of claim 12, wherein said ionic monomer is an amino-functional monomer.

17. The method of claim 16, wherein said amino-functional monomer is a vinylpyridine, an aminostyrene, an aminoacrylate or an aminomethacrylate.

18. The method of claim 1, wherein said monomer or mixture of monomers is gamma-irradiation induced polymerized in the substantial absence of oxygen.

* * * * *

UNITED STATES PATENT AND TRADEMARK OFFICE
CERTIFICATE OF CORRECTION

PATENT NO. : 5,376,400
DATED : December 27, 1994
INVENTOR(S) : Eugene P. GOLDBERG, ET AL It is certified that error appears in the above-identified patent and that said Letters Patent is hereby corrected as shown below:

Column 5, line 5: after "FIGS." insert -- 1, --.

Column 5, line 63: "craft" should read -- graft --.

Column 16, line 6: "(Goretex TM" should read -- (Goretex$^{TM}$) --.

Column 23, line 64 [Table 9, line 4]: in the heading for the fourth column, "% W, No" should read -- % $W_g$ No --.

Column 24, line 5 [Table 9, line 4]: in the heading for the fourth column, "% W, No" should read -- % $W_g$ No --.

Column 24, line 39 [Table 10, line 4]: in the heading for the fourth column, "% W, No" should read -- % $W_g$ No --.

Column 26, lines 26-27 [claim 11, lines 3-4]: "diemthylaminoethylmethacrylate" should read -- dimethylaminoethylmethacrylate --.

Signed and Sealed this

Twenty-first Day of March, 1995

Attest:

BRUCE LEHMAN

Attesting Officer    Commissioner of Patents and Trademarks